(12) United States Patent
Koenig

(10) Patent No.: US 6,946,966 B2
(45) Date of Patent: Sep. 20, 2005

(54) METHOD AND DEVICE FOR DIAGNOSING IN A MOTOR VEHICLE A DRIVER'S FITNESS DRIVE

(75) Inventor: Winfried Koenig, Pfinztal (DE)

(73) Assignee: Robert Bosch GmbH, Stuttgart (DE)

( * ) Notice: Subject to any disclaimer, the term of this patent is extended or adjusted under 35 U.S.C. 154(b) by 84 days.

(21) Appl. No.: 10/111,872

(22) PCT Filed: Aug. 28, 2001

(86) PCT No.: PCT/DE01/03232
§ 371 (c)(1),
(2), (4) Date: Jun. 17, 2002

(87) PCT Pub. No.: WO02/17786
PCT Pub. Date: Mar. 7, 2002

(65) Prior Publication Data
US 2003/0146841 A1 Aug. 7, 2003

(30) Foreign Application Priority Data
Aug. 29, 2000 (DE) .......................... 100 42 367

(51) Int. Cl.$^7$ .............................................. G08B 23/00
(52) U.S. Cl. ....................................... 340/576; 180/272
(58) Field of Search ................................. 340/576, 575; 180/272

(56) References Cited

U.S. PATENT DOCUMENTS

| | | | | |
|---|---|---|---|---|
| 4,664,127 A | * | 5/1987 | Ikeyama ..................... | 600/502 |
| 4,725,824 A | * | 2/1988 | Yoshioka ..................... | 340/575 |
| 4,928,090 A | * | 5/1990 | Yoshimi et al. ............. | 340/575 |
| 5,642,093 A | * | 6/1997 | Kinoshita et al. ........... | 340/439 |
| 5,813,989 A | * | 9/1998 | Saitoh et al. ................ | 600/484 |
| 5,821,860 A | * | 10/1998 | Yokoyama et al. ......... | 340/576 |
| 6,060,989 A | * | 5/2000 | Gehlot ........................ | 340/576 |
| 6,239,707 B1 | * | 5/2001 | Park ........................... | 340/576 |
| 6,313,749 B1 | * | 11/2001 | Horne et al. ................ | 340/575 |
| 6,575,902 B1 | * | 6/2003 | Burton ........................ | 600/300 |

FOREIGN PATENT DOCUMENTS

| | | |
|---|---|---|
| DE | 38 26 943 | 2/1990 |
| DE | 197 20 626 | 12/1997 |
| DE | 196 43 593 | 4/1998 |
| EP | 0 713 675 | 5/1996 |
| WO | WO 00/44580 | 8/2000 |

* cited by examiner

Primary Examiner—Thomas Mullen
(74) Attorney, Agent, or Firm—Kenyon & Kenyon

(57) ABSTRACT

A method is for diagnosing the driving capability of a driver of a motor vehicle, in which changes in driver condition are ascertained from physiological measured values derived from the driver while driving in the vehicle and evaluated, and if the changes are serious, a warning is issued or remedial actions are initiated, wherein the physiological measured values ascertained while driving in the vehicle are combined by a corresponding expert system with health-relevant data for the driver ascertained in stationary fashion, and with data indicating driver stress that are estimated in particular from the instantaneous traffic situation and instantaneous operating state of the vehicle, and the changes in the driver's condition are weighted with the estimated driver stress and interpreted. An apparatus for performing the method is characterized in that the expert system is implemented in an onboard computer of the vehicle which is connected via a bus internal to the vehicle to a mobile driver condition sensor suite that supplies the physiological measured values, to a memory/transfer medium that delivers the biographical data and/or the health-relevant data ascertained in stationary fashion, and to an ACC system and driving direction system internal to the vehicle.

26 Claims, 1 Drawing Sheet

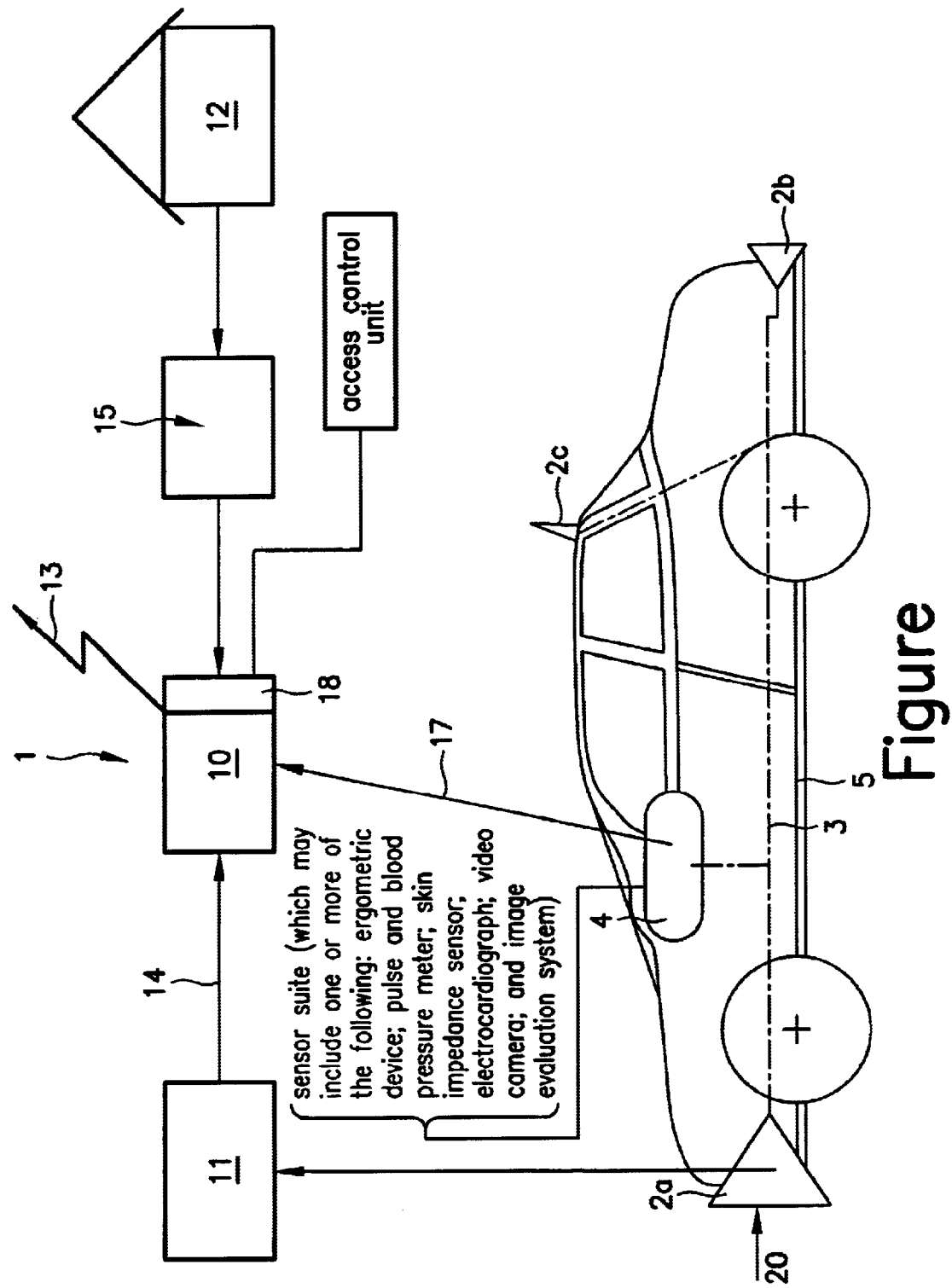

METHOD AND DEVICE FOR DIAGNOSING IN A MOTOR VEHICLE A DRIVER'S FITNESS DRIVE

FIELD OF THE INVENTION

The present invention relates to a method and apparatus for diagnosing the driving capability of a driver in a motor vehicle, in which changes in driver condition are ascertained from physiological measured values derived from the driver while driving in the vehicle, and if the changes are serious, a warning is issued or remedial actions are initiated.

BACKGROUND INFORMATION

Conventional systems which appraise the driver's condition on the basis of physiological parameters measured in the vehicle include, for example, interactive systems that request from the driver, while driving, certain input actions on the basis of which the driving capability of the driver is determined. Systems also exist which sense the eyelid blink frequency via a video camera with downstream image analysis. From the acquired blink frequency, conclusions can in turn be drawn regarding the driving capability of a driver in the motor vehicle.

Also available in the home context are systems, for example, exercise machines equipped with ergometric functions, which allow conclusions as to the health of the user by way of physiological measured values such as blood pressure, pulse rate, skin impedance, etc.

The informativeness of conventional systems or systems under development in terms of assessing the driving capability of the driver in a motor vehicle is considerably limited, however, by the fact that the only methods possible are those that do not use fixed electrodes or catheters on the driver's body, but instead must make do with contacts on bare skin areas or with entirely non-contact measurements, such as the aforesaid acquisition of the eyelid blink frequency a video camera.

SUMMARY

It is an object of the present invention to increase the reliability and informativeness of a method for diagnosing the driving capability of a driver of a motor vehicle in order, as applicable, to output to the driver a warning based on the diagnosis of driving capability and to initiate remedial actions if necessary.

According to an example embodiment of the present invention, the physiological measured values measured instantaneously while driving may be combined with stationary health-relevant data for the driver ascertained in the home context, and may be weighted and interpreted by an expert system with data, present in the vehicle or derived, indicating driver stress, in particular concerning the instantaneous traffic situation and the instantaneous vehicle operating state or changes in the driver's condition.

The data obtained in the vehicle from the vehicle operating state and from the instantaneous traffic situation may be used to derive an estimated value regarding the instantaneous driver stress, with which the instantaneous physiological data about the driver measured while driving in the vehicle, and the stationary health-relevant data obtained in the home context and combined therewith, may then be weighted and interpreted in a more informative fashion to yield a comprehensive appraisal of the driver's driving capability.

Circulatory data such as the driver's pulse rate and blood pressure may be particularly suitable for the acquisition of physiological values for the driver in the vehicle. Such circulatory data may easily be obtained with conventional transducers, for example, in the form of a wristwatch, and transmitted wirelessly to a receiver in the vehicle.

Also suitable may be a measurement in the vehicle of the driver's skin impedance. This physiological value may also be obtained using conventional transducers attached to the driver's skin, and transmitted wirelessly to a receiver in the vehicle.

As described previously, a video camera with downstream image processing may be used to measure an eyelid blink parameter, i.e., the driver's blink frequency and speed, which may provide clear information about driver fatigue.

An estimate of the instantaneous stress on the driver as a result of a situation in terms of driving, traffic, and the environment may be made from data that may be present in the vehicle or derivable. For example, data from a destination guidance system may be used. These may indicate the static traffic situation in which the driver finds him- or herself, e.g., urban, rural, at a complex intersection, on a narrow mountain road. Information regarding the dynamic traffic situation may be obtained from road condition data, weather data, and time of day; by using the sensed speed of the particular vehicle, for example acceleration values and frequency; and from the speed of other vehicles, for example based on ACC (Adaptive Cruise Control) signals. An estimate of the instantaneous traffic density, based on ACC data and using future video sensor apparatus, appears possible in principle.

In an example method according to the present invention, an estimate that is made of the instantaneous driver stress may be combined, by the use of an expert system, with the instantaneous physiological situation of the driver as supplied by the aforementioned physiological data acquired with the use of a driver condition sensor suite. As a result of this association, it may be possible to determine how the stress due to driving is reflected in the physiological data. It may be assumed in this context that other influences, for example, interaction with passengers or in conversations by mobile telephone in traffic, may have less of an influence on the driver's stress level. Stress resulting from driving may serve as an "ergometer" with which a patient, i.e., in this case, the driver, is brought into a known stress situation. The difference may also be that driving may represent more a mental and psychological stress than a physical one. From the physiological reaction of the driver's body to this stress, conclusions may then be drawn as the state of the driver's health. For example, extreme systolic blood-pressure values and rapid pulse rates may occur, and a determination may be made as to whether they are correlated with difficult traffic situations or are occurring without such stresses. In the latter case, the driver may be warned and may be advised to seek medical help. Information as to excessive fatigue or drugs (such as blood alcohol level) may be obtained in a conventional fashion from measured values of the driver condition sensor suite operated in the vehicle. As a result of this weighting with the driver stress estimated from the traffic situation and from the vehicle operating status, better conclusions may be drawn as to the relevance of this information.

In an example method according to the present invention, as mentioned, the instantaneous physiological data obtained using the mobile driver condition sensor suite in the vehicle may also be combined with health-relevant data for the driver ascertained on a stationary basis. Stationary health data of this kind may be ascertained, for example, using home-based systems that are capable of obtaining from the user's (in this case the driver's) biological material, such as urine, feces, sweat, etc., information about the person's state of health. Health-relevant data may also be collected and stored in home health devices, for example bicycle ergometers, exercise machines, blood-sugar measurement instruments, scales, etc.

These stationary data may be obtained in static situations or during muscle work, and not under predominantly mental/psychological stress such as may occur in a motor vehicle. The stationary data may be stored in a suitable storage/transfer medium, and the latter may be read by an input arrangement in the vehicle or the stored information may be sent to a receiver in the vehicle. This memory/transfer medium may be, for example, a chip card, a wristwatch with wireless transmission technology, a mobile radio system, etc.

The expert system in the motor vehicle may weight the instantaneous physiological data (obtained while driving using the mobile driver condition sensor suite) with the driver's health-relevant data obtained in stationary fashion, and thereby may obtain a more comprehensive picture of the driver's state of health, so that in the event of serious deviations from normal values, remedial actions may be initiated as applicable.

In the event no stationary measured values concerning the driver's state of health in the home context may be obtained, standard values may be assumed by the diagnostic method according to the present invention, and those standard values may be refined using inputted biographical data such as the driver's gender, age, and weight.

In an example embodiment, an expert system may be set up as a learning system. Initially, before a valid diagnosis as to driving capability is issued, a learning phase with at least one test drive by the driver may be performed in the vehicle, including a variety of stress levels and traffic situations.

An apparatus configured to perform the example method may contain the expert system implemented in an onboard computer of the vehicle, and the onboard computer may be connected via a vehicle bus system to the driver condition sensor suite which supplies the physiological measured values; to a memory/transfer arrangement that delivers the biographical data and/or health-relevant data ascertained in stationary fashion; to an arrangement that estimates the driver stress based on the instantaneous traffic situation and the instantaneous vehicle operating state and transmits it to the onboard computer; and also an arrangement that imparts to the driver as a warning signal, or that emits to the environment, a signal indicating an overload or a driver stress that is not appropriate for the situation. An ACC system and a vehicle navigation system may be used to ascertain the instantaneous traffic situation and to appraise the driver stress. In order to identify the driver, the onboard computer and the expert system residing therein may be connected to a vehicle access authorization control unit.

BRIEF DESCRIPTION OF THE DRAWING

FIG. 1 is a schematic view of a system according to the present invention.

DETAILED DESCRIPTION

The description below describes, with reference to the functional block diagram illustrated in FIG. 1, steps of an example driver diagnosis method according to the present invention, as well as functions of an example embodiment of an apparatus configured to perform the method.

System 1, illustrated in FIG. 1 in the form of functional blocks, includes the following functional units:
- an expert system 10 implemented in an onboard computer;
- an ACC and navigation system 11 having associated sensors 2a, 2b and a radio antenna 2c;
- an arrangement 12 for acquiring the stationary (at-home) physiological data of a driver;
- arrangements 15, 18 for storing/transferring to the onboard computer the health-relevant data obtained in stationary fashion;
- a vehicle bus system 3 for connecting various units in the vehicle; and
- a driver condition sensor suite 4 located in vehicle 5.

An optionally provided driver access authorization control unit is not illustrated.

Sensors 2a, 2b associated with ACC and navigation system 11, and radio antenna 2c, serve to acquire environmental/traffic situation 20, for example, via radar waves, video image acquisition, and/or ultrasonic waves, and to receive driving direction information via GSM mobile radio. In ACC and navigation system 11, ACC information 20 acquired by the corresponding sensors 2a, 2b and antenna 2c—for example, the number, speed, and heading of other vehicles, and driving direction information; also the vehicle's own heading and speed, road category, urban/rural, weather data, road condition, topographic data, etc.—is ascertained, and the driver stress is estimated therefrom and transmitted in the form of a signal 14 to expert system 10 in the onboard computer. Expert system 10 also receives, from mobile driver condition sensor suite 4 (which may include an electrocardiogram or electrocardiograph), signals 17 that indicate the physiological data for the driver in the vehicle acquired by driver condition sensor suite 4. The physiological data ascertained in stationary home-based system 12, as well as biographical data, are inputted via memory/transfer medium 15 (i.e., a chip card), using an input/read medium 18, into expert system 10. In the latter, the stationary health data thus inputted are combined with the instantaneous physiological data 17 for the driver acquired by mobile driver condition sensor suite 4 while driving, weighted with estimated value 14 for driver stress, and interpreted.

Expert system 10 weights the physiological and biographical data with the estimated driver stress 14 and, if the changes in driver condition are serious, generates a warning for the driver and/or a signal 13, e.g., emittable externally via GSM radio, which indicates the overload or situationally inappropriate stress on the driver so that remedial actions may be initiated. In one example embodiment, the onboard computer or expert system may be connected to a driver access authorization control unit which performs the identification of the driver and delivers it to the expert system.

The core of the example method according to the present invention, and of the example embodiment of an apparatus according to the present invention configured to perform the example method, is thus the combination, performed by the expert system, of physiological data 17 (obtained while driving via driver condition sensor suite 4) with the stationary health-relevant data obtained in the home context and delivered via memory/transfer medium 15, and the weighting of these combined data using an estimated value 14 that indicates driver stress, which is estimated as an independent variable based on the traffic situation and driving direction information obtained from the onboard ACC and navigation system 11 and is delivered to expert system 10. From the weighted change in driver condition, expert system 10 decides if that change is so serious that driving capability is questionable, if a warning signal needs to be issued to the driver, or if applicable remedial actions need to be initiated.

In the example embodiment described above, expert system 10 resides in an onboard computer of a vehicle 5. The example method according to the present invention is not, however, limited to this example embodiment, but rather may also be usable if expert system 10 resides outside vehicle 3 at a central location, to which the physiological data ascertained by way of the mobile driver condition sensor suite, the stationary physiological and biographical data, and the information about the traffic situation and the driving direction information ascertained from the ACC system and navigation system 11 are then conveyed.

As described above, the present invention may be applied to ascertain the driving capability of the driver of a motor vehicle. It may nevertheless be apparent to those skilled in this art that the present invention may also be applicable to operating capability diagnosis in the context of drivers (or pilots) of other vehicles and a mode of transportation, for example ships, aircraft, and rail vehicles. The term "motor vehicle" or "vehicle" used herein is thus to be construed broadly.

What is claimed is:

1. A method for diagnosing a driving capability of a driver of a motor vehicle, comprising the steps of:
   ascertaining health-relevant data for the driver obtained while the driver is stationary;
   acquiring physiological measured values for the driver while driving in the vehicle;
   combining, by an expert system, the physiological measured values with the health-relevant data;
   ascertaining changes in a driver condition from the combined physiological measured values and health-relevant data;
   estimating a variable indicating a driver stress from data that is one of present and derived in the vehicle concerning an instantaneous traffic situation and an instantaneous vehicle operating state;
   weighting and interpreting, by the expert system, the changes in the driver condition with the variable indicating a driver stress in order to detect if the driver is in an impaired condition; and
   one of issuing a warning and initiating remedial actions to counteract the driver condition if the weighted and interpreted changes in the driver condition fulfill at least one predetermined criterion pertaining to the impaired condition.

2. The method of claim 1, wherein the physiological measured values include circulatory measured values.

3. The method of claim 2, wherein the circulatory measured values include a pulse rate and a blood pressure of the driver in the vehicle.

4. The method of claim 1, wherein the physiological measured values acquiring step includes the substep of sensing an impedance of a skin of the driver, the physiological measured values including the impedance.

5. The method of claim 1, wherein the physiological measured values acquiring step includes the substep of measuring an electrocardiogram of the driver, the physiological measured values including the electrocardiogram.

6. The method of claim 1, wherein the physiological measured values acquiring step includes the substep of sensing an eyelid blink frequency of the driver, the physiological measured values including the eyelid blink frequency.

7. The method of claim 1, wherein the health-relevant data include physiological data measured while the driver is stationary and biographical data.

8. The method of claim 7, wherein the physiological data include ergometric data measured on an ergometric device.

9. The method of claim 7, wherein the biographical data include at least one of an age, a weight, and a gender.

10. The method of claim 7, wherein if the physiological data measured while the driver is stationary are not present or are not measurable, the health-relevant data include standard values refined using inputted biographical data.

11. The method of claim 10, wherein the inputted biographical data includes a gender, an age, and a weight.

12. The method of claim 1, wherein the health-relevant data include blood analysis values of the driver.

13. The method of claim 12, wherein the blood analysis values include a blood sugar level.

14. The method of claim 1, further comprising the step of calculating the driver stress from a combination of the instantaneous traffic situation and instantaneous operating state data for the motor vehicle, the instantaneous traffic situation estimated from the number, speed, and heading of other vehicles and from relevant driving direction information for the vehicle, the instantaneous operating state data including a heading and a speed of the vehicle.

15. The method of claim 1, further comprising the step of initially performing at least one test drive by the driver during a learning phase before a valid diagnosis of the driving capability is issued, wherein a learning system is used as the expert system, the test drive including a variety of stress levels and traffic situations.

16. An apparatus for diagnosing a driving capability of a driver of a motor vehicle, comprising:
   a vehicle-based driver condition sensor suite configured to supply physiological measured values;

a memory/transfer arrangement configured to deliver at least one of biographical and health-relevant data, the data ascertained while the driver is stationary;

a traffic/vehicle monitor arrangement configured to ascertain and transfer an instantaneous traffic situation and an instantaneous operating data of the motor vehicle to an onboard computer of the motor vehicle;

a transmission arrangement configured to transfer a signal to an environment, the signal indicating a driver stress that is inappropriate for the instantaneous traffic situation;

an expert system arranged in the onboard computer; and a vehicle bus arranged to connect the onboard computer to the vehicle-based driver condition sensor suite, the memory/transfer arrangement, the traffic/vehicle monitor arrangement, and the transmission arrangement.

17. The apparatus according to claim 16, wherein the vehicle-based driver condition sensor suite includes a pulse and blood-pressure meter.

18. The apparatus according to claim 16, wherein the vehicle-based driver condition sensor suite includes a skin impedance sensor.

19. The apparatus according to claim 16, wherein the vehicle-based driver condition sensor suite includes an electrocardiograph.

20. The apparatus according to claim 16, wherein the vehicle-based driver condition sensor suite includes a video camera with a downstream image evaluation system configured to sense and evaluate the driver's eyelid blink frequency.

21. The apparatus according to claim 16, wherein the memory/transfer arrangement includes a memory medium and an input/read apparatus connected to the onboard computer and configured to read the memory medium.

22. The apparatus according to claim 21, wherein the memory medium includes a chip card.

23. The apparatus according to claim 16, wherein the traffic/vehicle monitor arrangement includes an ACC system and a vehicle navigation system connected to corresponding sensors.

24. The apparatus according to claim 16, wherein the transmission arrangement includes a radio transmission system.

25. The apparatus according to claim 24, wherein the radio transmission system includes a GSM mobile data radio system.

26. The apparatus according to claim 16, wherein the onboard computer is connected to an access control unit of the vehicle, the access control unit configured to perform an identification of the driver.

* * * * *

UNITED STATES PATENT AND TRADEMARK OFFICE
CERTIFICATE OF CORRECTION

PATENT NO. : 6,946,966 B2 Page 1 of 1
APPLICATION NO. : 10/111872
DATED : September 20, 2005
INVENTOR(S) : Winifried Koenig It is certified that error appears in the above-identified patent and that said Letters Patent is hereby corrected as shown below:

Title Page, Item (54), line 3, change "FITNESS DRIVE" to --FITNESS TO DRIVE--

Column 1, line 3, change "FITNESS DRIVE" to --FITNESS TO DRIVE--

Signed and Sealed this

Second Day of October, 2007

JON W. DUDAS
*Director of the United States Patent and Trademark Office*